United States Patent [19]
Reinecke et al.

[11] 3,984,149
[45] Oct. 5, 1976

[54] COMPRESSED AIR BRAKING SYSTEM

[75] Inventors: Erich Reinecke, Beinhorn; Heinrich Blase, Wunstorf, both of Germany

[73] Assignee: WABCO Westinghouse GmbH, Germany

[22] Filed: July 28, 1975

[21] Appl. No.: 600,180

[30] Foreign Application Priority Data
Aug. 1, 1974 Germany............................ 2437027
Oct. 1, 1974 Germany............................ 2446773

[52] U.S. Cl. .................................. 303/7; 188/3 R; 303/71; 303/84 R
[51] Int. Cl.² ........................................ B60T 13/38
[58] Field of Search ................ 303/7, 9, 13, 2, 6 R, 303/84, 68, 69, 71, 40, 28; 188/3

[56] References Cited
UNITED STATES PATENTS
3,285,672  11/1966  Avrea ..................................... 303/9
3,294,455  12/1966  Valentine................................ 303/9
3,504,946  4/1970  Valentine et al. ...................... 303/9
3,713,702  1/1973  Campanini............................. 303/9

*Primary Examiner*—Trygve M. Blix
*Assistant Examiner*—Douglas C. Butler
*Attorney, Agent, or Firm*—Ken C. Decker; William N. Antonis

[57] ABSTRACT

A fluid pressure braking system for an articulated vehicle wherein the system includes a supply line and a service brake line interconnecting the tractor and trailer portions of the vehicle. A trailer control valve controls communication through the service brake line. A throttle valve is located in the supply line, and is adapted to restrict communication therethrough when the pressure differential across the trailer control valve exceeds a predetermined level during a brake application.

9 Claims, 3 Drawing Figures

COMPRESSED AIR BRAKING SYSTEM

This invention relates to a compressed-air two-circuit brake system for articulated motor vehicles having a tractor and trailer with a two-line trailer connection.

In motor vehicles of this kind, the braking system is so constituted that the compressed-air connection to the trailer consists of a supply line and a service brake line. In case of a rupture in the trailer service brake line, the supply line is vented during braking via the rupture point in the service line and the trailer is thus braked via the supply line and the trailer emergency braking system. But because the air pressure in the tractor reservoirs must first of all drop to the predetermined actuating pressure of the three-circuit protective valve and the overflow valve, about 6–8 seconds are required in this type of braking system before the pressure in the supply line drops below the predetermined pressure and the trailer is braked. As a consequence of this long time interval there is a danger that, in case of full braking, only the tractor will brake while the brake system of the trailer will not respond, or will respond much too late which, in the case of a heavily loaded trailer, would mean that the trailer would push the tractor, and the tractor-trailer combination would jack-knife.

One already known device provides a valve inserted between the three-circuit protective valve and the trailer coupling of the supply line. This valve blocks the supply line in case of a rupture in the trailer service brake line when a brake application is effected. This device, however, entails the great disadvantage that, when hitching up a trailer with empty air reservoirs, the valve prevents charging of the trailer brake system when, during the hitching process, the brake system of the motor vehicle must be actuated at the same time — something which could be the case, for example, when hitching up along an incline. If the truck-trailer combination is braked fully, after a short driving distance, which is not long enough to charge the trailer brake system, there is a danger — especially during downhill driving — that the trailer might push the tractor and the tractor-trailer combination might jack-knife, which can have devastating consequences.

One object of the invention is, in case of a rupture in the trailer service brake line, to reduce the pressure in the supply line below a predetermined low pressure level, within less than 2 seconds, which is tantamount to the response time of the trailer braking system. Another object of the invention is to eliminate the above-described disadvantage which may occur when a valve is used while hitching up a trailer.

According to the invention, this problem is solved by providing a controllable throttle in the line between the three-circuit protective valve and the trailer coupling of the supply line. This throttle is so designed that, during normal driving operation, uninhibited communication of compressed air into the trailer braking system is permitted and the throttle is actuated only when a predetermined pressure differential is exceeded due to a rupture in the trailer service brake line when a brake application is effected. The throttle diameter is selected so that substantially more compressed air flows off via the rupture point than is supplied via the throttle in order to reduce the pressure level in the trailer braking system to below the predetermined level. On the other hand, enough compressed air must be allowed to pass through the throttle when the braking system is working properly to fill the trailer's brake system under all conditions.

The throttle is made as a controllable throttle because it is necessary for this throttle to be turned on only during braking when the trailer service brake line has broken or when it is not hitched up. If the trailer service brake line is in order and if it is hitched up, the throttle must not be turned on so that the braking pressure may be built up within a prescribed time, which can be attained only if the unthrottled cross-section is available within the throttle valve.

The invention will now be described in greater detail with the help of the drawings. Known devices and pertinent lines which are not required for an understanding of the invention have been omitted for the sake of greater clarity.

DETAILED DESCRIPTION OF THE PREFERRED EMBODIMENT

Figure 1:
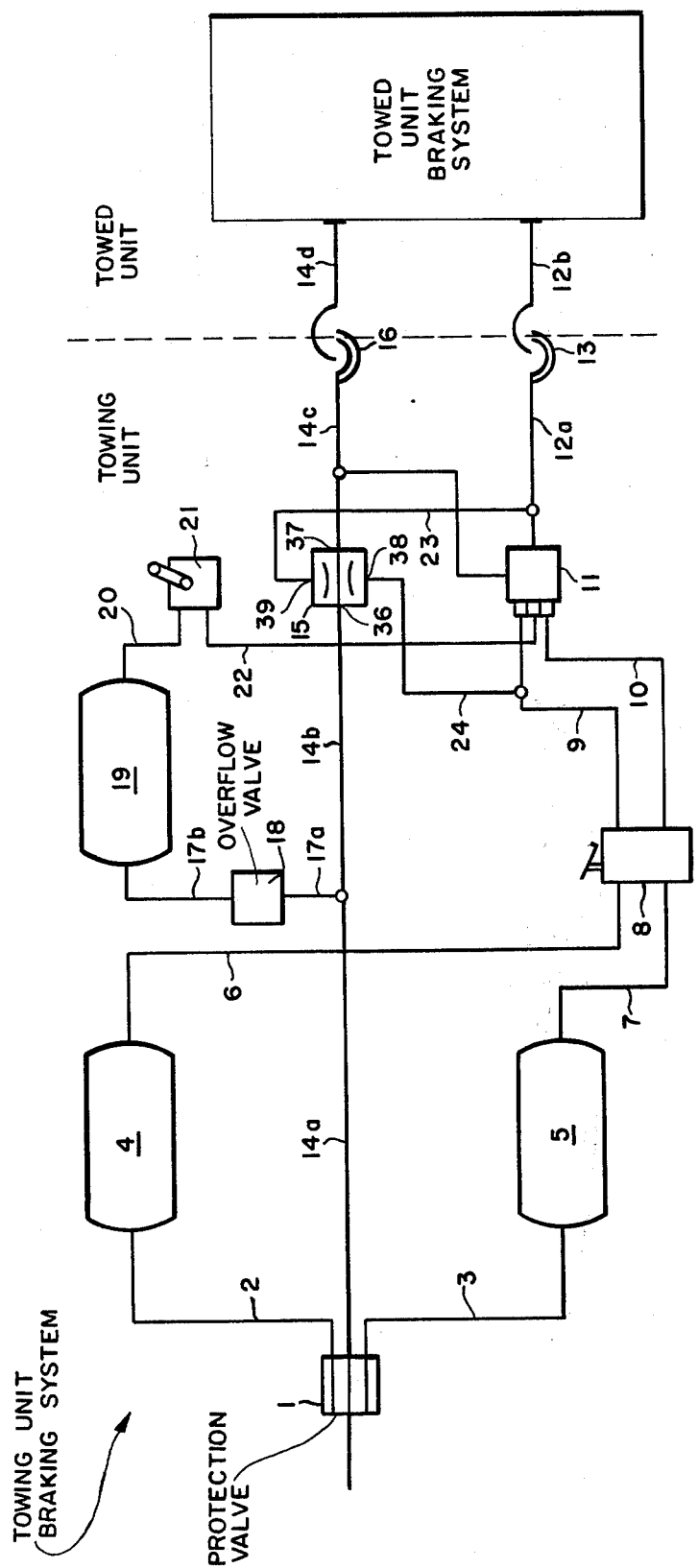
FIG. 1 is a schematic illustration of a braking system made pursuant to the teachings of our invention.

The compressed air required for the operation of the brake system is generated by an air compressor, not illustrated, which is connected via a three-circuit protective valve 1 and via the lines 2 and 3 with the reservoirs 4 and 5. From these reservoirs, lines 6 and 7 lead to the two-circuit motor vehicle brake valve 8 and the lines 9 and 10 on to the trailer control valve 11, to which is connected the trailer service brake line 12 with the trailer coupling 13. Valve 11 controls communication through conduit 12a, 12b to control actuation of the service brakes on the trailer. From the third circuit of the three-circuit protective valve, supply lines 14a and 14b lead via connections 36 and 37 of the throttle valve 15, made according to the invention, and via line 14c to the automatic coupling head 16. The supply line 14d communicates air pressure to charge the supply reservoir carried by the trailer and also communicates air pressure to the trailer emergency braking system between lines 14a and 14b there branches off, before the throttle valve, the line 17a which charges the reservoir 19 with compressed air via the overflow valve 18 and line 17b. From this tank, line 20 leads to the hand brake valve 21 and via line 22 to the trailer control valve 11. The control connection 39 of the throttle valve is connected via line 23 with the trailer serivce brake line 12, and line 24 connects the control connection 38 of the throttle valve with line 9, which connects the two-circuit brake valve 8 with the trailer control valve 11.

During normal driving operation, the compressed air has unhindered passage to the trailer through the throttle valve 15 via connections 36 and 37 because identical pressure conditions prevail in lines 23 and 24 so that the spring 28 holds the piston 26 with plunger 29 firmly in the position illustrated. Only in case of a rupture in the trailer service brake lines 12a and 12b is the tension of spring 28 overcome, due to the pressure difference arising in lines 23 and 24, and the throttle 32 is then engaged. The throttling of the compressed-air throughout thus achieved means that the supply line is vented via the rupture point in the service brake line, so that within two seconds after the throttle 32 is engaged, the pressure level in the trailer drops below the predetermined pressure level and the trailer emergency braking system is actuated.

DETAILED DESCRIPTION OF THE ALTERNATE EMBODIMENT

Figure 2:
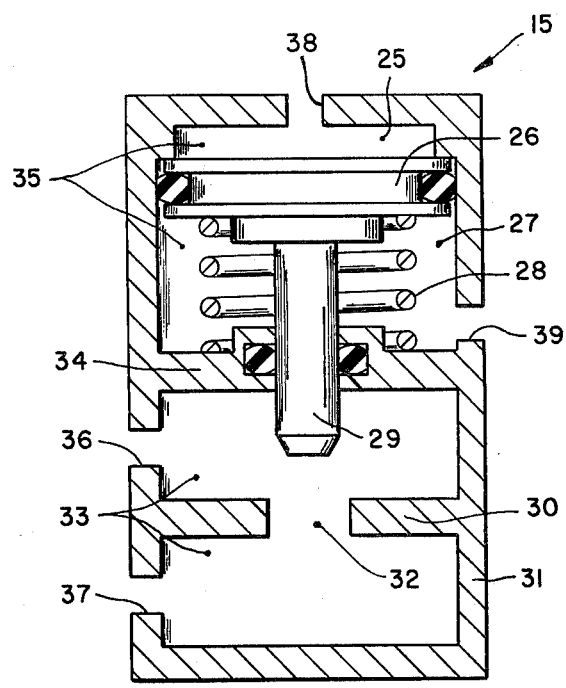
FIG. 2 is a cross-sectional view of one embodiment of a throttle valve used in the braking system illustrated in FIG. 1.
Figure 3:
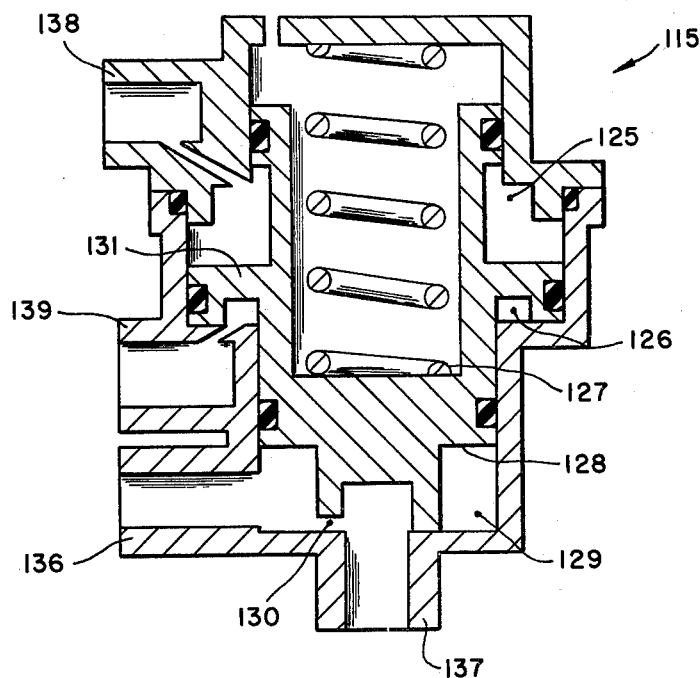
FIG. 3 is a view similar to FIG. 2, but illustrating another embodiment of the throttle valve used in our invention.

In the embodiment of FIG. 2, the piston and plunger of the throttle valve is motionless during normal driving operation. Because its function is triggered only in emergencies, for example, in case of a break in the trailer brake line, there is a danger that the piston of the control element might stick due to corrosion and might not work in case of danger. In the embodiment of FIG. 3, the throttle valve is controlled in such a way that the control element is moved during normal driving operation. This is accomplished by moving the control element due to the fluctuations in the operating pressure without influencing the actual function of the throttle valve.

In contrast to the throttle valve described in the embodiment of FIG. 2 — where a prestressed spring keeps the control element in operating position — the prestressed spring in the embodiment of FIG. 3 is provided to insure that the control element will be moved to the throttle position. A force arising from operating pressure and through the surface impacted by this operating pressure works against this spring force whereby the piston surface and the spring force are so dimensioned that the force, which emerges from the lowest operating pressure on the piston surface, is a little larger than the prestressing spring when the throttle is engaged. Due to the fluctuations in operating pressure, the control element is now constantly moved to a limited extent during normal driving operations without moving into a throttling position. The piston is moved into the throttle position, limited by the stop, only when the service brake line is ruptured.

Furthermore, the throttle valve according to the embodiment of FIG. 3 is so designed that most of the piston surfaces impacted by the operating pressure will be upstream of the throttle. This surface is dimensioned so large that, if the pressure drops below operating pressure in the valve outlet connection — which is possible in case of the sudden connection of a pressureless trailer — the throttle will not be completely engaged. If the largest part of the piston surface were to be located downstream of the throttle point, then a brief pressure drop below operating pressure would lead to the full engagement of the throttle until the compressed air system of the trailer is charged through the small throttle cross-section. The time for charging a trailer brake system would exceed the time allowed by law.

Referring now to FIG. 3, compressed air can pass unhindered through the throttle valve 115 via connections 136 and 137, because the force, arising from operating pressure and the impacted piston surface 128 in chamber 129, lifts the piston 131 from its throttle position against the tension of the spring 127 into the unthrottled operating position. Every fluctuation in the operating pressure during normal driving operation brings about a constant movement of the piston 131 without the piston moving into the throttling position in the process. At the same time, identical pressure conditions prevail in the control lines 23 and 24, which are connected with the connections 138 and 139 of the throttle valve, as well as with chamber 125 above piston 131 and with chamber 126 beneath the piston, so that the movements of piston 131 will not influence the supply line pressure during normal driving operation. Only in case of a rupture in the trailer service brake lines 12a and 12b will there be a pressure difference during braking between the lines 23 and 24. When a rupture occurs, line 23 and thus chamber 126 are vented via the rupture point while pressure will build up during braking in line 24. The pressure building up simultaneously in chamber 125 now moves the piston 131 down and engages the throttle 130 which consists of a recess along the frontal surface of the piston. The throttling of the compressed air throughout thus achieved now brings about a ventilation of the supply line 14c within 2 seconds below the predetermined pressure level and thus makes it possible to brake the trailer.

What is claimed is:

1. In a fluid pressure braking system for an articulated vehicle having a towed unit and a towing unit, each of said units having a braking system, a supply line interconnecting said units for communicating fluid pressure from the towing unit to the towed unit, a service line interconnecting said units for controlling the braking system on the towed unit, control valve means having an inlet communicated to the braking system on the towing unit and an outlet communicated through said service line to the braking unit on the towed unit, said control valve means controlling communication through said service line, and a throttle valve in said supply line shiftable from a first condition permitting substantially uninhibited fluid communication through said supply line to a second condition restricting communication through said supply line, said throttle valve including pressure differential responsive means connected to the inlet and outlet of the control valve means for shifting said throttle valve from said first condition to said second condition when the pressure differential between the inlet and the outlet of said control valve means during braking exceeds a predetermined amount.

2. The invention of claim 1, said throttle valve including a housing having an inlet and an outlet each connected in said supply line, a passage communicating the inlet with the outlet, a piston slidably mounted in said housing and shiftable toward and away from a position restricting communication through said passage as the throttle valve is shifted from the first to the second condition, said pressure differential responsive means being connected to said piston for actuating the latter.

3. The invention of claim 2:
said pressure differential responsive means being a pair of opposed faces on said piston, one of said faces being communicated to said service line at one side of said control valve means, the other face being communicated to said service line at the other side of said control valve means.

4. The invention of claim 3, and
resilient means yieldably urging said piston away from the position restricting communication through said passage.

5. The invention of claim 3:
said housing including a partition extending between said inlet and outlet, said passage including an aperture in said partition adapted to receive said piston when the latter is shifted to its position restricting communication through said passage, whereby said piston cooperates with the wall of the aperture to define a flow-restricting orifice therebetween.

6. The invention of claim 3; and resilient means yieldably urging said plunger toward said position restricting communication through the passage.

7. The invention of claim 6:
said piston including a portion adapted to cooperate with the wall of said housing at an area between the inlet and outlet to define a flow-restricting orifice.

8. The invention of claim 6:
said piston defining a face exposed to the fluid pressure level at said inlet.

9. The invention of claim 6:
said piston defining a face exposed to the fluid pressure level upstream of said orifice.

* * * * *